US009955289B1

(12) United States Patent
Liu et al.

(10) Patent No.: US 9,955,289 B1
(45) Date of Patent: Apr. 24, 2018

(54) SYSTEMS AND METHODS FOR IMPLANTABLE MEDICAL DEVICES INCLUDING NEAR FIELD COMMUNICATIONS

(71) Applicant: PACESETTER, INC., Sylmar, CA (US)

(72) Inventors: Franklin Liu, Porter Ranch, CA (US); Jorge N. Amely-Velez, Simi Valley, CA (US); Perry Li, Arcadia, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/265,624

(22) Filed: Sep. 14, 2016

(51) Int. Cl.
| | |
|---|---|
| *H04B 5/00* | (2006.01) |
| *H04W 4/00* | (2018.01) |
| *A61N 1/02* | (2006.01) |
| *A61N 1/362* | (2006.01) |
| *A61N 1/372* | (2006.01) |
| *A61N 1/39* | (2006.01) |
| *H04B 5/02* | (2006.01) |
| *H01Q 1/27* | (2006.01) |
| *H01Q 1/24* | (2006.01) |

(52) U.S. Cl.
CPC ............ *H04W 4/008* (2013.01); *A61N 1/025* (2013.01); *A61N 1/362* (2013.01); *A61N 1/37229* (2013.01); *A61N 1/3956* (2013.01); *H01Q 1/243* (2013.01); *H01Q 1/273* (2013.01); *H04B 5/0025* (2013.01); *H04B 5/0062* (2013.01); *H04B 5/02* (2013.01); *H04M 2250/02* (2013.01); *H04M 2250/04* (2013.01)

(58) Field of Classification Search
CPC ............ H04W 4/008; H04W 52/0225; H04W 52/0251; H04B 5/00; H04B 5/0025; H04B 5/0062; H04B 5/0075; H04M 2250/02; H04M 2250/04; A61N 1/37211; A61N 1/37252; A61N 1/37276
USPC .................. 455/41.1, 41.2, 574, 343.1, 343.2
See application file for complete search history.

(56) References Cited

U.S. PATENT DOCUMENTS

| | | | | |
|---|---|---|---|---|
| 8,068,057 | B2 * | 11/2011 | Yamagajo | G06K 19/07786 340/572.7 |
| 8,954,030 | B1 * | 2/2015 | Buchheit | A61N 1/3925 455/404.1 |
| 9,288,614 | B1 * | 3/2016 | Young | A61N 1/37252 |
| 9,431,694 | B2 * | 8/2016 | Li | H01Q 1/273 |
| 2003/0137461 | A1 * | 7/2003 | Peng | H01Q 1/243 343/702 |
| 2004/0260363 | A1 * | 12/2004 | Arx | A61N 1/37252 607/60 |
| 2007/0018832 | A1 * | 1/2007 | Beigel | G06K 19/07345 340/572.7 |

(Continued)

*Primary Examiner* — Duc M Nguyen

(57) ABSTRACT

The present disclosure provides a near field communications (NFC) detector network for use in an implantable medical device. The NFC detector network includes a combined Bluetooth low energy (BLE)NFC antenna, a BLE transceiver, a BLE path electrically connecting the combined BLE/NFC antenna to the BLE transceiver and configured to communicate BLE signals received at the combined BLE/NFC antenna to the BLE transceiver, and an NFC path electrically connecting the combined BLE/NFC antenna to the BLE transceiver, the NFC path configured to generate an activation signal for the BLE transceiver based on an NFC signal received at the combined BLE/NFC antenna.

8 Claims, 7 Drawing Sheets

(56) References Cited

U.S. PATENT DOCUMENTS

| | | | | |
|---|---|---|---|---|
| 2008/0143487 A1* | 6/2008 | Hulvey | ............. | G06F 13/24 |
| | | | | 340/10.34 |
| 2008/0231530 A1* | 9/2008 | Rao | ............. | H01Q 9/0407 |
| | | | | 343/767 |
| 2010/0045441 A1* | 2/2010 | Hirsch | ............. | H04B 5/0012 |
| | | | | 340/10.1 |
| 2010/0203831 A1* | 8/2010 | Muth | ............. | H02J 17/00 |
| | | | | 455/41.2 |
| 2011/0070825 A1* | 3/2011 | Griffin | ............. | H04B 5/0031 |
| | | | | 455/41.1 |
| 2011/0250841 A1* | 10/2011 | Hulvey | ............. | H04B 5/0062 |
| | | | | 455/41.1 |
| 2012/0034867 A1* | 2/2012 | Griffin | ............. | H04W 52/0254 |
| | | | | 455/41.1 |
| 2012/0313830 A1* | 12/2012 | Lee | ............. | H01Q 1/243 |
| | | | | 343/729 |
| 2013/0109309 A1* | 5/2013 | Desclos | ............. | H04B 5/0075 |
| | | | | 455/41.1 |
| 2013/0241784 A1* | 9/2013 | Wong | ............. | H01Q 9/14 |
| | | | | 343/749 |
| 2014/0220885 A1* | 8/2014 | Chou | ............. | H04W 4/008 |
| | | | | 455/41.1 |
| 2016/0359222 A1* | 12/2016 | Li | ............. | H01Q 1/273 |

\* cited by examiner

SYSTEMS AND METHODS FOR IMPLANTABLE MEDICAL DEVICES INCLUDING NEAR FIELD COMMUNICATIONS

FIED OF THE DISCLOSURE

The present disclosure relates generally to implantable medical devices, and, more particularly, to circuitry for activating components of an implantable medical device using near field communications.

BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all HF patients suffer debilitating symptoms immediately. Some may live actively for years. Yet, with few exceptions, the disease is relentlessly progressive. As HF progresses, it tends to become increasingly difficult to manage. Even the compensatory responses a triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for HF is typically centered around medical treatment using ACE inhibitors, diuretics, and digitalis. It has also been demonstrated that aerobic exercise may improve exercise tolerance, improve quality of life, and decrease symptoms. Cardiac surgery has also been performed on a small percentage of patients with particular etiologies. Although advances in pharmacological therapy have significantly improved the survival rate and quality of life of patients, some HF patients are refractory to drug therapy, have a poor prognosis and limited exercise tolerance. In recent years cardiac pacing has emerged as an effective treatment for many patients with drug-refractory HF.

Implantable medical devices used to treat HF include, for example, pacemakers, cardiac monitors, and cardioverter-defibrillators. Such implantable devices are designed to communicate with external devices, for example, to program or reprogram the implanted devices, or to receive data from the implanted medical devices.

The wireless communication modes used in at least some known implantable devices provide less than optimal energy consumption for certain applications. Accordingly, a need exists for implantable medical devices configured to communicate with external devices via lower-power communication modes. For example, Bluetooth Low Energy (BLE) communications may be used in an implantable medical device. However, because a BLE transceiver consumes power when active, it may be desirable to place the BLE transceiver in a sleep or inactive mode until communication is necessary. In order to activate the BLE transceiver from a sleeping state, a method of sending a wakeup signal from an external programmer to the implantable medical device may be implemented. For example, U.S. patent application Ser. No. 14/969,589, filed Dec. 15, 2015 (which is incorporated by reference herein in its entirety) describes receiving a near field communications (NFC) signal from an external programmer, and using that NFC signal to activate the BLE transceiver.

However, circuitry for detecting and processing BLE communications does not typically include simple circuitry for detecting NFC signals (e.g., at 13.56 megahertz (MHz)). Instead NFC integrated circuits are often relatively complex, as they are designed to process data transmissions. Therefore, such integrated circuits consume large amounts of current.

BRIEF SUMMARY OF THE DISCLOSURE

In one embodiment, the present disclosure is directed to a near field communications (NFC) detector network for use in an implantable medical device. The NFC detector network includes a combined Bluetooth low energy (BLE)/NFC antenna, a BLE transceiver, a BLE path electrically connecting the combined BLE/NFC antenna to the BLE transceiver and configured to communicate BLE signals received at the combined BLE/NFC antenna to the BLE transceiver, and an NFC path electrically connecting the combined BLE/NFC antenna to the BLE transceiver, the NFC path configured to generate an activation signal for the BLE transceiver based on an NFC signal received at the combined BLE/NFC antenna.

In another embodiment, the present disclosure is directed to an implantable medical device. The implantable medical device includes a housing, a cover coupled to the housing and enclosing a region along an exterior of the housing, and a near field communications (NFC) detector network. The NFC detector network includes a combined Bluetooth low energy (BLE)/NFC antenna positioned in the region, a BLE transceiver, a BLE path electrically connecting the combined BLE/NFC antenna to the BLE transceiver and configured to communicate BLE signals received at the combined BLE/NFC antenna to the BLE transceiver, and an NFC path electrically connecting the combined BLE/NFC antenna to the BLE transceiver, the NFC path configured to generate an activation signal for the BLE transceiver based on an NFC signal received at the combined BLE/NFC antenna.

In another embodiment, the present disclosure is directed to a method for activating a Bluetooth low energy (BLE) transceiver in an implantable medical device. The method includes receiving a near field communication (NFC) signal at a combined BLE/NFC antenna, preventing the NFC from reaching the BLE transceiver via a BLE path that electrically connects the combined BLE/NFC antenna to the BLE transceiver, generating, using an NFC path that electrically connects the combined BLE/NFC antenna to the BLE transceiver, an activation signal based on the NFC signal, and activating the BLE transceiver using the activation signal.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The embodiments described herein provide a near field communication (NFC) detector network for an implantable medical device that is capable of using Bluetooth Low Energy (BLE) communications and NFC. In the systems and methods described herein, a voltage detector is activated in the presence of an NFC field and triggers BLE circuitry to activate (or wakeup) to begin normal operations. The detection techniques described herein are passive, and accordingly, consume essentially no current. Therefore, the entire BLE activation process may be achieved with minimum drain on a battery of the implantable medical device, extending the longevity of the battery.

Figure 1:
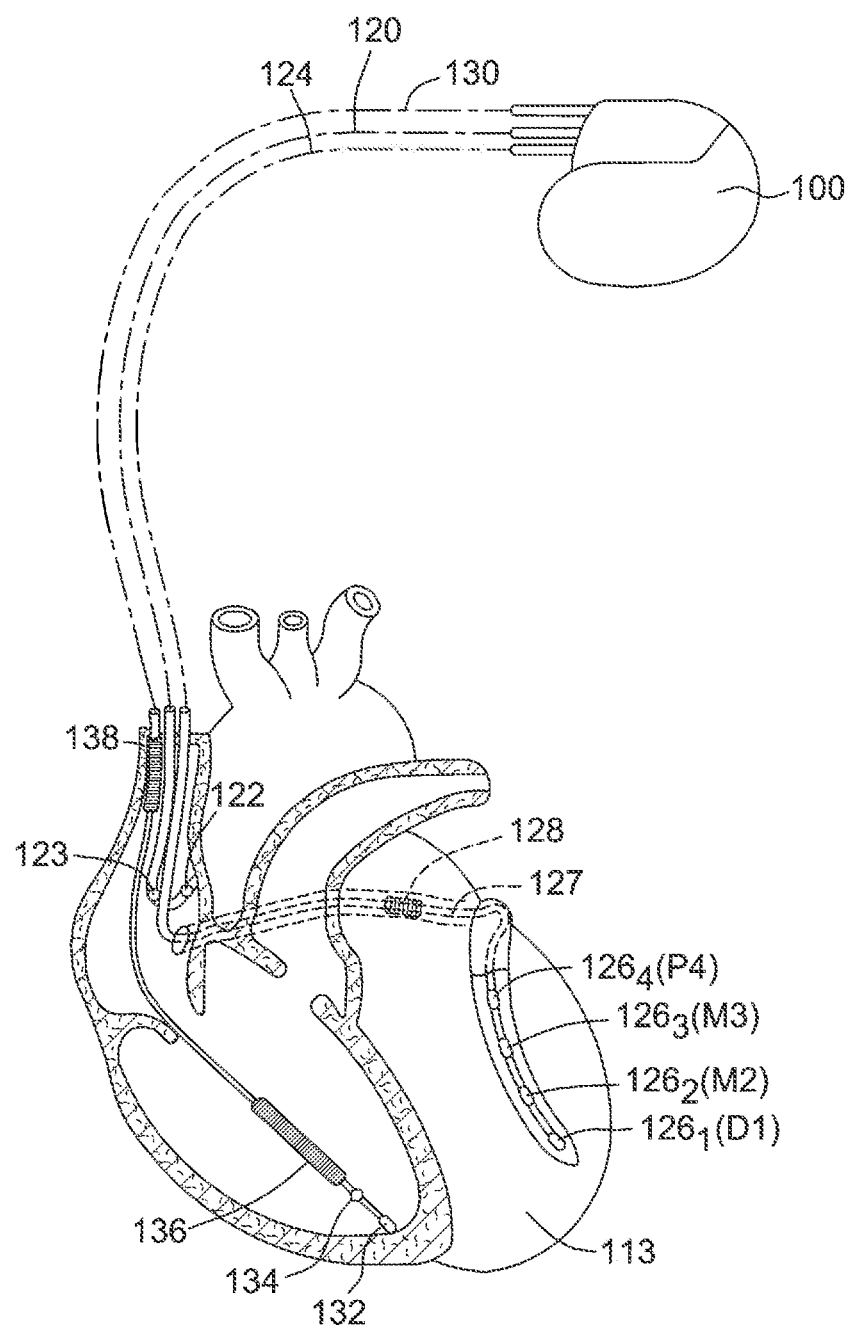
FIG. 1 is a simplified, partly cutaway view illustrating an implantable stimulation device in electrical communication with at least three leads implanted into a patient's heart for delivering multi-chamber stimulation and shock therapy and sensing cardiac activity.
Figure 2:
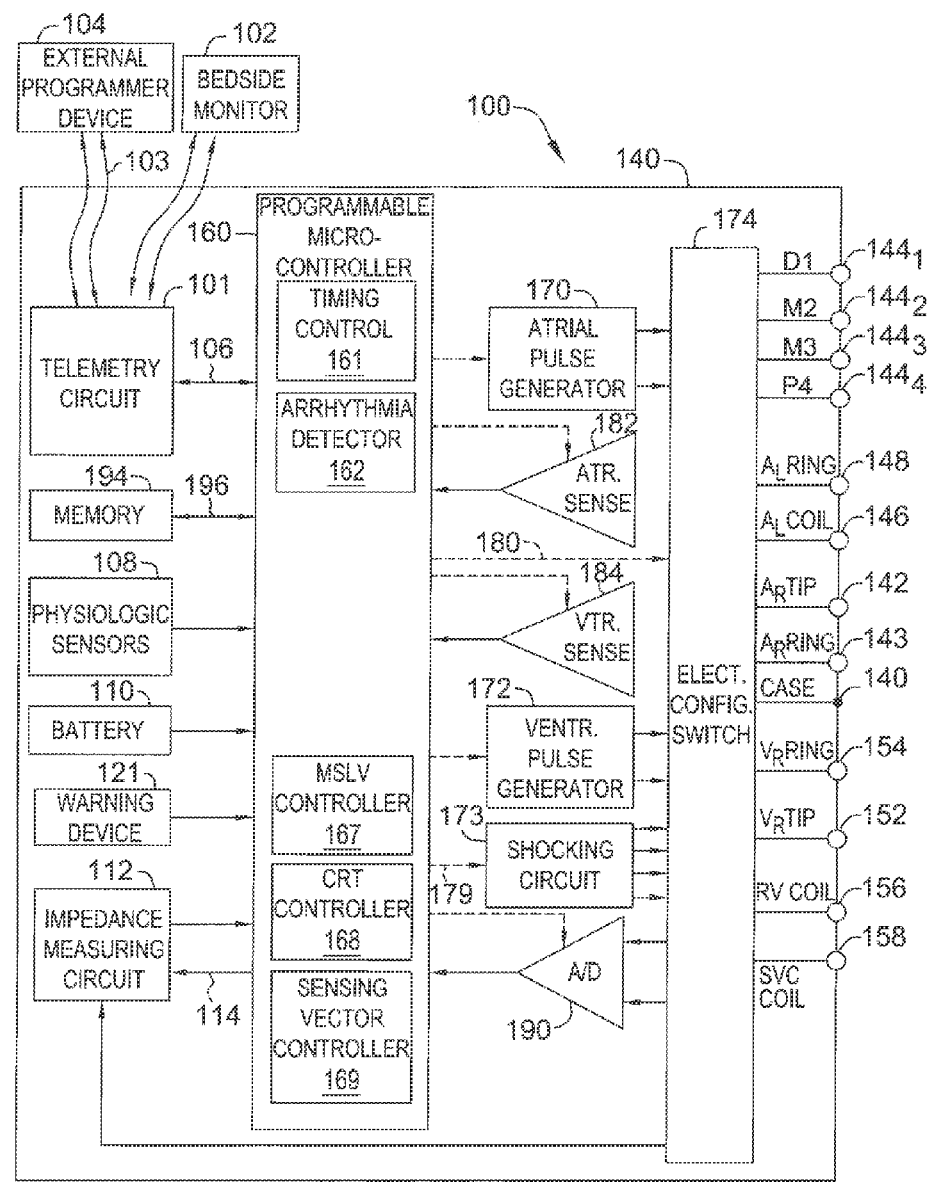
FIG. 2 is a functional block diagram of the multi-chamber implantable stimulation device of FIG. 1, illustrating the basic elements that provide pacing stimulation, cardioversion, and defibrillation in four chambers of the heart.

Referring now to the drawings, and, in particular, to FIGS. 1 and 2, one embodiment of an implantable medical device shown in the form of a pacemaker/implantable cardioverter-defibrillator (CD) 100, is indicated generally at 100. Although reference is made herein to a pacemaker/ICD, embodiments of the present disclosure are suitable for use with implantable medical devices other than pacemakers/ICDs including, for example and without limitation, cardiac monitors.

FIG. 1 is a simplified diagram of pacemaker/ICD 100, which is a dual-chamber stimulation device capable of treating both fast and slow arrhythmias with stimulation therapy, including cardioversion, defibrillation, and pacing stimulation, including multi-site left ventricular (MSLV) pacing. To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a RV tip electrode 132, a RV ring electrode 134, a RV coil electrode 136, and a superior vena cave (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e,g., the Quartet™ left ventricular pacing lead developed by St. Jude Medical Inc. (headquartered in St. Paul, Minn.), which includes four pacing electrodes on the left ventricular lead—enabling up to ten pacing configurations LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ ((i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e,g., vectors between an LV electrode and RV coil electrode 136). Below is a list of example vectors that can be used for pacing and/or sensing using LV electrodes D1, M2, M3 and P4 with and without RV coil electrode 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4

M2→P4
M3→M2
M3→P4
P4→M2

Alternative and/or additional vectors, other than those listed above, can be used for pacing and/or sensing. Although only three leads are shown in FIG. 1, it should also be understood that additional leads (with one or more pacing, sensing, and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 2. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 2, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 (shown in FIG. 1) for shocking purposes. Housing 140 further includes a connector (not shown) having a plurality of terminals, 142, 143, 144$_1$-144$_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal (A$_R$ TIP) 142 adapted for connection to the atrial tip electrode 122 and an RA ring terminal (A$_R$ RING) electrode 143 adapted for connection to RA ring electrode 123. To achieve left chamber sensing, pacing and shocking, the connector includes an LV tip terminal 144$_1$ adapted for connection to the D1 electrode and additional LV electrode terminals 144$_2$, 144$_3$ and 144$_4$ terminals adapted for connection to the M2, M3 and P4 electrodes of quadra-pole LV lead 124.

The connector also includes an LA shocking terminal (A$_L$ COIL) 146 and an LA ring terminal (A$_L$ RING) 148, which are adapted for connection to LA ring electrode 127 and the LA coil (A$_L$ COIL) electrode 128, respectively. To support right chamber sensing, pacing and shocking, the connector further includes an RV tip terminal (V$_R$ TIP) 152, an RV ring terminal (V$_R$ RING) 154, an RV shocking terminal (V$_R$ COIL) 156, and an SVC shocking terminal (SVC COIL) 158, which are adapted for connection to RV tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 2, an atrial pulse generator 170 and a ventricular pulse generator 172 generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (VV) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc.

Microcontroller 160 further includes an arrhythmia detector 162 that can be utilized by the pacemaker/ICD 100 for determining desirable times to administer various therapies. Additional components of the microcontroller include a MSLV controller 167 to control the actual delivery of MSLV pacing and a cardiac resynchronization therapy (CRT) controller 168 to control CRT, which can be performed in conjunction with MSLV pacing.

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode, to achieve the various sensing vectors that are used to obtain IEGMs in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. For example, the MSLV controller and the CRT controller 168 can be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 182 and ventricular sensing circuits 184 may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190. Data acquisition system 190 is configured to acquire intracardiac electrogram signals, convert the raw analog data into a digital signal, and store the digital signals for later processing and/or telemetric transmission to an external programmer or device 104 or a personal advisory module (PAM) or bedside monitor 102. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable dataiaddress bus 196, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external device 104 or bedside monitor 102, such as a programmer, transtelephonic transceiver, or a diagnostic system analyzer. The telemetry circuit 101 is activated by the microcontroller by a control signal 106, and includes suitable components for wirelessly communicating with external device 104 and bedside monitor 102 including, for example and without limitation, transceivers, antennas, and combinations thereof. Telemetry circuit 101 advantageously allows intracardiac electrograms and status information relating to the operation of pacemaker/ICD 100 (as contained in microcontroller 160 or memory 194) to be sent to external device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICD additionally includes a battery 110 that provides operating power to the circuits shown in FIG. 2. As further shown in FIG. 2, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV coil electrode 136, or as part of a split electrical vector using SVC coil electrode 138 or LA coil electrode 128 (i.e., using RV coil electrode 136 as a common electrode).

Pacemaker/ICD 100 is provided as an example. One or ordinary skill in the art would understand that embodiments described herein can be used with alternative types of implantable devices including, for example and without limitation, implantable cardiac monitors and implantable neuromodulation devices. Accordingly, embodiments described herein should not be limited to use only with the above described device.

Figure 3:
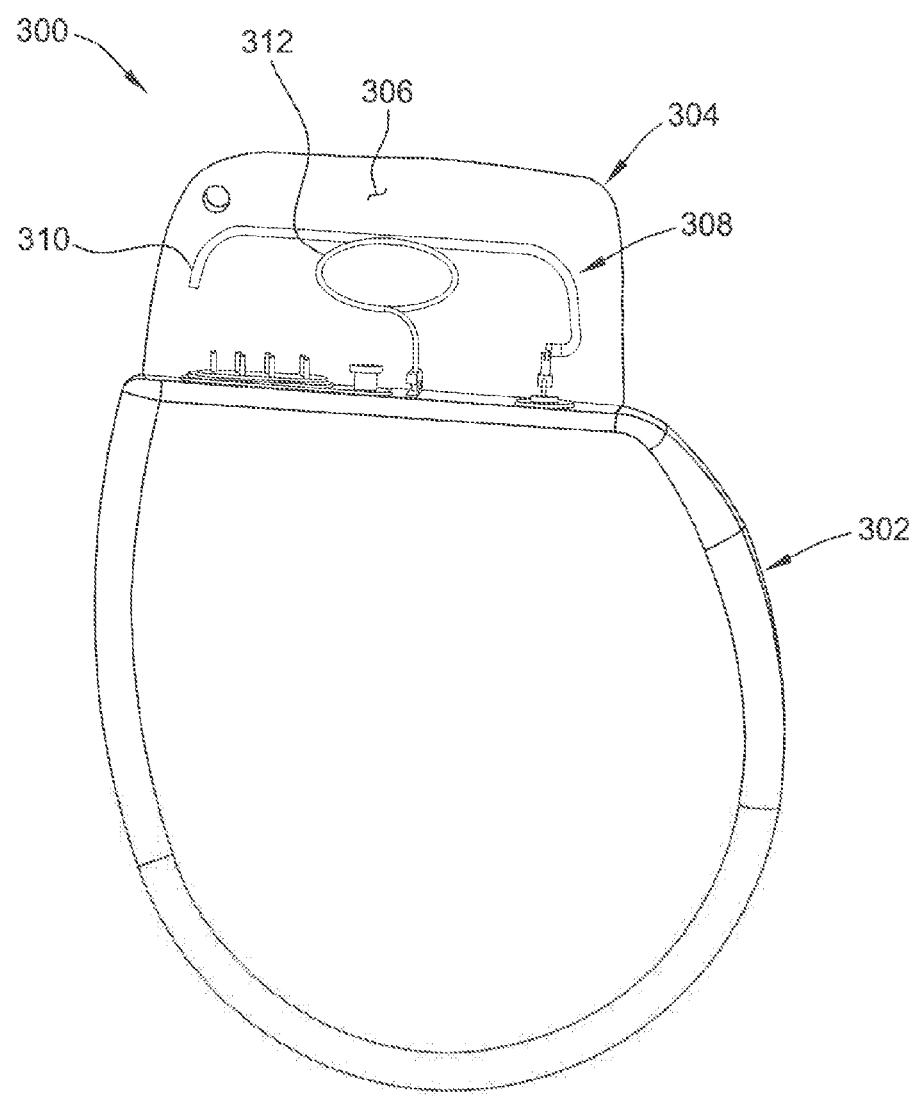
FIG. 3 is a side view of one embodiment of an implantable medical device including a dual-purpose antenna structure.

FIG. 3 is a side view of one embodiment of an implantable medical device 300 suitable for use as pacemaker/ICD 100 shown and described above with reference to FIGS. 1 and 2. As shown in FIG. 3, implantable medical device 300 includes a housing 302, a cover 304 coupled to an exterior of housing 302 and enclosing a region 306 along the exterior of housing 302, and a dual-purpose antenna structure 308 disposed within region 306. As described in more detail herein, dual-purpose antenna structure 308 is configured to receive wireless signals within a low-frequency band (e.g., a near-field communication (NFC) band) and a high-frequency band (e.g., a Bluetooth or Bluetooth Low Energy (BLE) band) to enable efficient, low-power operation of device 300.

Although not shown in FIG. 3, device 300 also includes components and circuitry enclosed within housing 302 to enable operation of device 300, as described in detail herein. Also, certain components enclosed within cover 304 are omitted from FIG. 3. Device 300 may include any and/or all of the components of pacemaker/ICD 100 described above with reference to FIGS. 1 and 2. For example, device 300 includes a programmable microcontroller, such as a microcontroller 160 (shown in FIG. 2), and a telemetry circuit, such as telemetry circuit 101 (shown in FIG. 2), to enable wireless communication with and programming of the microcontroller.

Housing 302 is sealed and is designed to protect components of device 300 from damage and other environmental conditions. Housing 302 may also act as the return electrode for various operating modes of device (e.g., "unipolar" modes). Housing 302 may further be used as a return electrode alone or in combination with one or more coil electrodes, such as coil electrodes 128, 136 and 138 described above with reference to FIGS. 1 and 2, for shocking purposes. Additionally, as described in more detail herein, housing 302 may be used as a ground terminal for antenna structure 308. As such, housing 302 is constructed from a suitably conductive, biocompatible material, including, for example and without limitation, titanium, although housing 302 may be constructed from other suitable conductive, biocompatible materials.

As noted above, cover 304 encloses region 306 located along exterior of housing 302. Region 306 may be referred to as the "device header". Cover 304 is constructed from a suitably biocompatible material, and may be constructed from electrically insulative or nonconductive materials. Suitable materials from which cover 304 may be constructed include, for example and without limitation, epoxy.

Antenna structure 308 is disposed on exterior of housing 302 and within region 306 enclosed by cover 304. Antenna structure 308 is positioned outside of housing 302 to avoid interference between housing 302 and antenna structure 308. Antenna structure 308 is electrically coupled to telemetry circuit 101 and/or programmable controller 160 for sending signals received from external devices to telemetry circuit 101 and/or programmable controller 160, and for transmitting signals from implantable device 300 to external devices.

As noted above, antenna structure 308 is a dual-purpose antenna structure configured to receive wireless signals within a low-frequency band (e.g., a near-field communication (NFC) band) and a high-frequency band (e.g., a Bluetooth or BLE band) to enable efficient, low-power operation of device 300. Specifically, in this embodiment, antenna structure 308 enables communication over a BLE network while also enabling BLE components of device 300 to be activated and powered off or deactivated when not in use through use of NFC signals.

Traditionally, BLE transceivers and associated components consume power when on, even when not actively communicating with another device. Accordingly, use of BLE components in at least some known implantable medical devices presents a drawback due to the finite power capacity of batteries used in such devices. Antenna structures of the present disclosure overcome these drawbacks by enabling use of a sleep or inactive mode with BLE components, such as transceivers. For example, BLE components, such as transceivers, can be placed into a sleep or inactive mode until communication is necessary to reduce power consumption. However, using a sleep or inactive mode requires a low power method of bringing the BLE components out of the sleep or inactive mode. The antenna structures described herein provide a low power method of activating BLE components by enabling a wakeup or activation signal to be received at the implanted device from an external device (e.g., a programmer) through use of near-field communications (NFC) signals. To receive communication signals within different frequency bands, the antenna structures of the present disclosure include two antennas, each dedicated to receiving signals within a certain frequency range, and connected to one another in such a way such that each antenna does not interfere with operation of the other.

In this embodiment, antenna structure 308 includes a first antenna 310 configured to receive wireless signals within a first frequency band (e.g., a Bluetooth or BLE band), and a second antenna 312 configured to receive wireless signals within a second frequency band lower than the first frequency band (e.g., a NFC band).

In this embodiment, first antenna 310 is configured to transmit and receive signals within a Bluetooth or BLE frequency band, specifically, 2.45 gigahertz (GHz). In other embodiments, first antenna 310 may be configured to receive signals other than signals within a Bluetooth or BLE frequency band, and may have any suitable length that enables device 300 to function as described herein.

First antenna 310 is constructed from a suitably conductive, biocompatible material. Moreover, first antenna 310 may be constructed from a suitably ductile material to enable a length of first antenna 310 to be adjusted by manipulating first antenna 310. Suitable materials from which first antenna 310 may be constructed include, for example and without limitation, titanium.

In this embodiment, second antenna 312 is configured to receive NFC signals at a frequency of approximately 13.5 megahertz (MHz). Near-field communication generally involves communication between electromagnetically or wirelessly coupled devices over short distances, such as distances less than 40 cm, less than 20 cm, and distances less than 10 cm. Near-field communication signals are typically on the order of tens of MHz. Embodiments of antenna structures disclosed herein are particularly suitable for use with NFC signals in a frequency band of 13.5 MHz. Due to the frequencies at which NFC operates, second antenna 312 cannot be placed in housing 302 because the conductive housing would shield and/or interfere with NFC signals. Accordingly, in this embodiment, second antenna 312 is located outside housing 302 within region 306 enclosed by cover 304 (i.e., the device header).

Size restrictions within region 306 prohibit second antenna 312 from having an optimal antenna length for use with NFC signals, which is typically on the order of several meters. Accordingly, in this embodiment, second antenna 312 is designed to operate based on the principal of inductive communication. Additional details of device 300 are described in U.S. patent application Ser. No. 14/969,589, filed Dec. 15, 2015, which is incorporated by reference herein in its entirety.

Device 300 also includes signal detection and communications circuitry configured to detect signals received by second antenna 312 (e.g., NFC signals), and to transmit and receive signals using first antenna 310 (e.g., BLE signals). For example, telemetry circuit 101 includes NFC detection circuitry and BLE communications circuitry, as described herein. In one embodiment, telemetry circuit 101 includes a BLE integrated circuit (IC) having integrated NFC detection capability. In another embodiment, telemetry circuit 101 includes a separate NFC detection circuit formed from discrete components.

Figure 4:
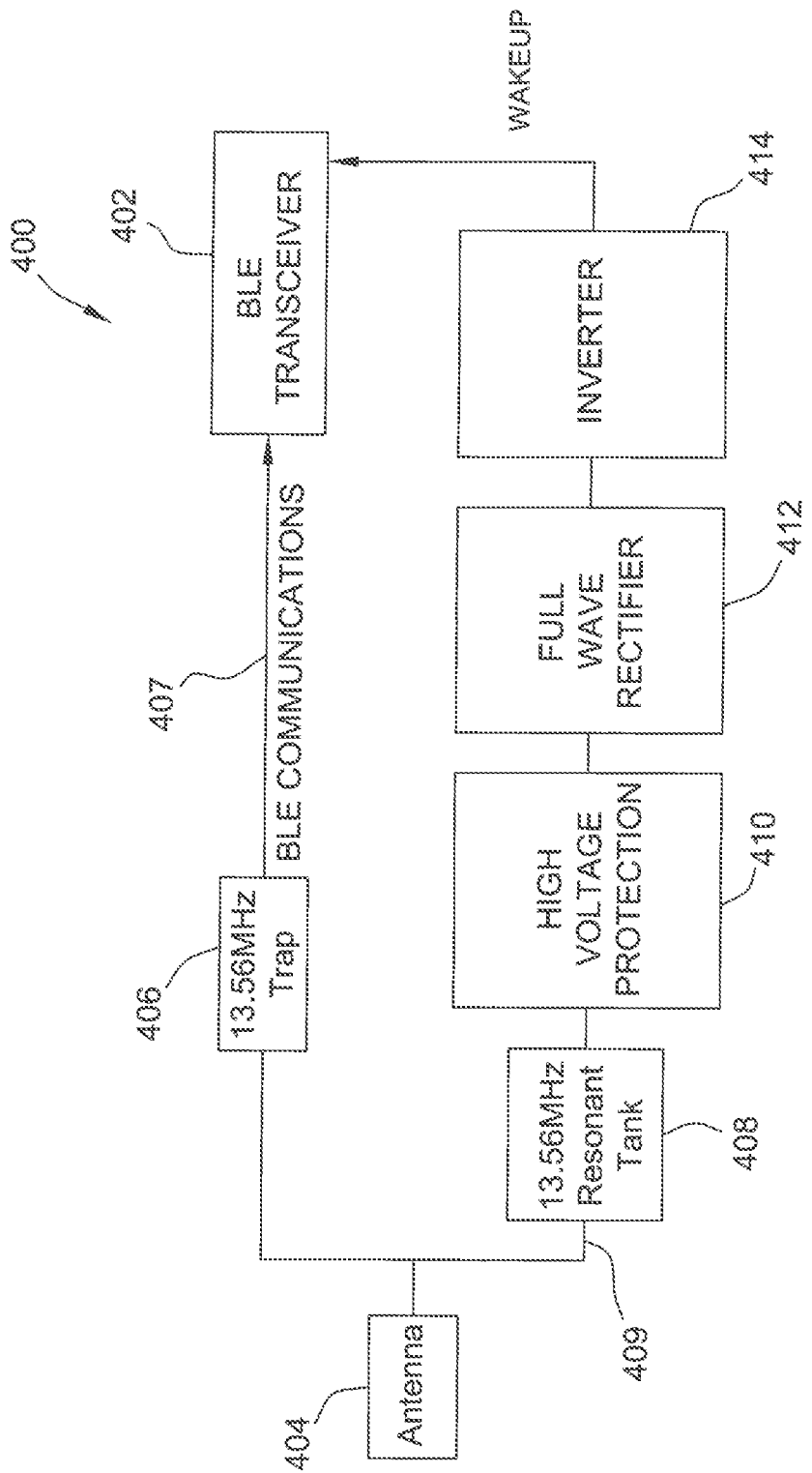
FIG. 4 is a block diagram of one embodiment of a detector network that may be used with the device shown in FIG. 3.
Figure 5:
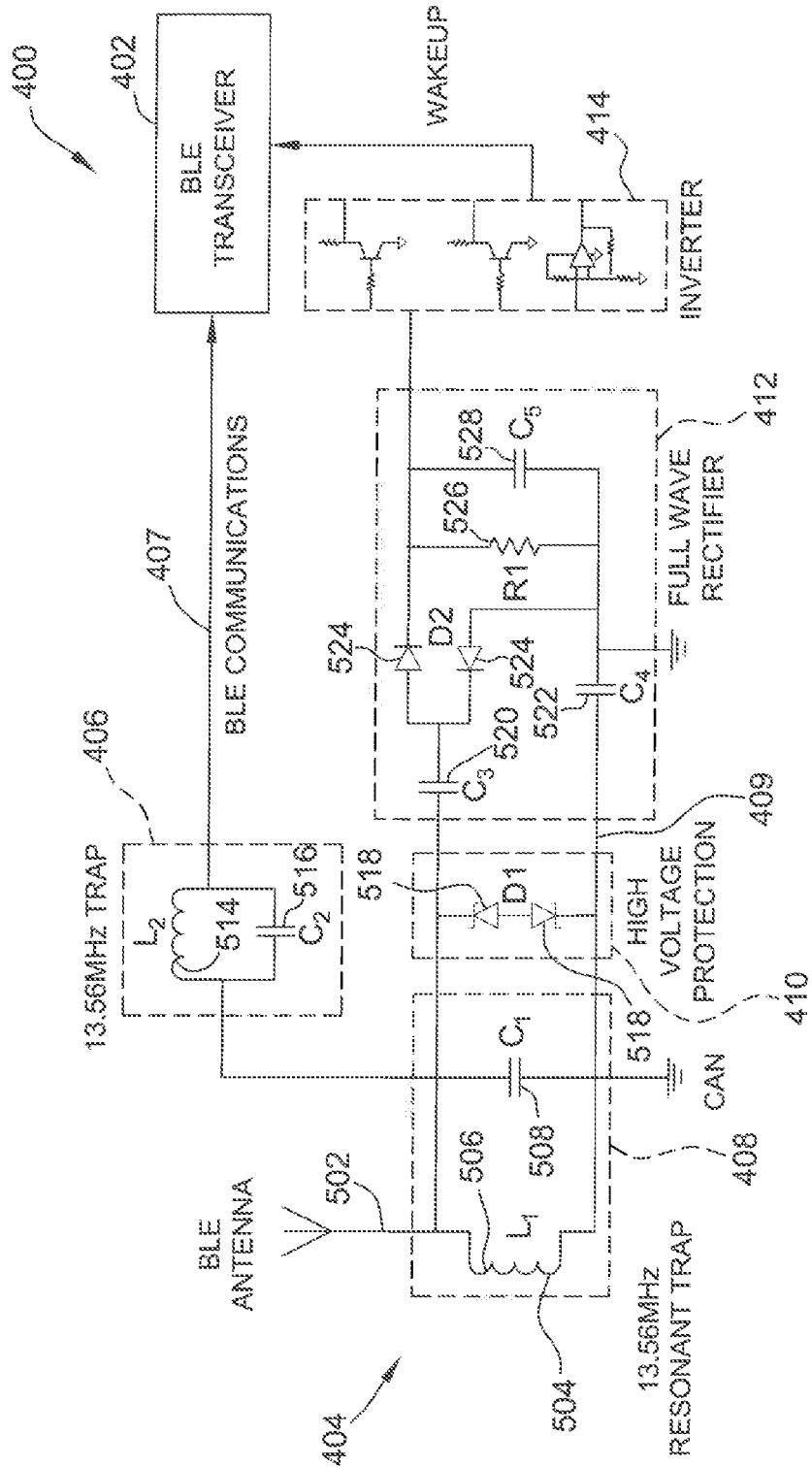
FIG. 5 is a schematic circuit diagram of the detector network shown in FIG. 4.

FIG. 4 is a block diagram of one embodiment of a detector network 400 that may be used with device 300. FIG. 5 is a schematic circuit diagram of detector network 400. As described herein, detector network 400 facilitates detecting an NFC signal and converting the NFC signal into a form that may be used to activate a BLE transceiver 402 from a sleep mode.

As shown in FIGS. 4 and 5, detector network 400 includes a combined BLE/NFC antenna 404, such as antenna structure 308 (shown in FIG. 3). In this embodiment, antenna 404 receives a 13.56 MHz NFC signal. After being received at antenna 404, a 13.56 MHz trap 406 on a BLE path 407 blocks the NFC signal from entering a frontend of BLE transceiver 402. This facilitates ensuring that none of the NFC signal mixes into BLE communications as noise.

Detector network 400 also includes a 13.56 MHz resonant tank 408 on an NFC path 409 that draws the NFC signal. Because detector network 400 is intended for signals less than 5 volts(V), a high voltage protection circuit 410 is included in detector network 400 to protect against relatively large NFC fields (e.g., NFC fields found in electronic surveillance equipment).

In this embodiment, a full-wave rectifier 412 converts the NFC signal into a DC signal that is used to activate BLE transceiver 402. To activate BLE transceiver 402, the NFC signal should have an amplitude high enough to ensure activation of the BLE transceiver 402 from a distance of at least 5 centimeters (cm). To satisfy this, full-wave rectifier 412 also maximizes the amplitude of the incoming NFC signal while filtering out any residual AC signal that remains following the rectification. In some embodiments, the output of full-wave rectifier 412 may be used directly to activate BLE transceiver 402. However, BLE transceiver 402 may require an activation signal having an amplitude of at least 1.8 V with a negative edge trigger. Accordingly, in this embodiment, an inverter 414 conditions the output of full-wave rectifier 412 to provide a final activation, or wakeup, signal to BLE transceiver 402.

Notably, the components of detector network 400 are passive, which allows detecting the NFC signal and activating BLE transceiver 402 with relatively low battery drain. This is possible because detector network 400 does not use any signal processing or commmication techniques, but instead uses the voltage waveform of the signal itself to trigger the activation. As long as the NFC signed has a sufficient voltage amplitude for detector network 400 to detect the NFC signal, the NFC signal may have any modulation or composition. This allows the wakeup method described herein to be implemented using conventional smart devices (e.g., mobile communication devices) that have NFC capabilities already built-in for functions such as NFC tag detection, wireless payment, etc. To eliminate unintentional activations of BLE transceiver 402, appropriate firmware may be installed on such smart devices.

As described above, detector network 400 receives an NFC signal and converts it into a form that BLE transceiver 402 can recognize as an activation signal. As shown in FIG. 5, in this embodiment, combined BLE/NFC antenna 404 includes a BLE antenna 502 coupled to an NFC antenna 504. Accordingly, combined BLE/NFC antenna 404 is able to capture both NFC and BLE signals. Detector network 400 includes BLE path 407 for BLE signals and NFC path 409 for NFC signals.

NFC antenna 504 is implemented as a first inductor 506 in this embodiment. First inductor 506 cooperates with a first capacitor 508 to form resonant tank 408 on NFC path 409. The value of first capacitor 508 is chosen such that resonant tank 408 resonates at 13.56 MHz. Accordingly, at resonance, the voltage fed into NFC path 409 is a maximum. As shown in FIG. 5, BLE path 407 includes 13.56 MHz trap 406 that blocks the NFC signal from entering a frontend of BLE transceiver 402. 13.56 MHz trap 406 is implemented using a second inductor 514 electrically coupled in parallel with a second capacitor 516.

NFC signals may have a small signal form (e.g., mobile communication devices, NFC tags) or a large signal form (e.g., large-scale NFC readers). Accordingly, high voltage protection circuit 410 prevents high voltage damage to detector network 400 from large NFC signals. In this embodiment, high voltage protection circuit 410 includes a pair of Zener diodes 518.

As shown in FIG. 5, full-wave rectifier 412 includes a third capacitor 520 and a fourth capacitor 522 that function as blocking capacitors. Full-wave rectifier 412 also includes a pair of Schottky diodes 524 connected as a voltage doubler, a resistor 526, and a fifth capacitor 528. Schottky diodes 524 rectify the NFC signal, and resistor 526 and fifth capacitor 528 form a low pass filter to remove any residual AC signal.

Figure 6A:
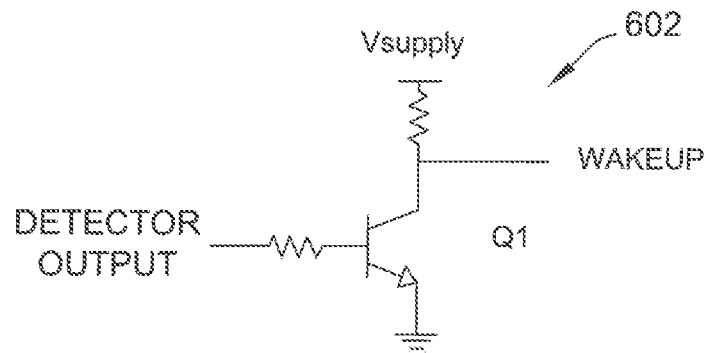
FIGS. 6A and 6B are schematic circuit diagrams of embodiments of inverters that may be used with the detector network shown in FIGS. 4 and 5.
Figure 6B:
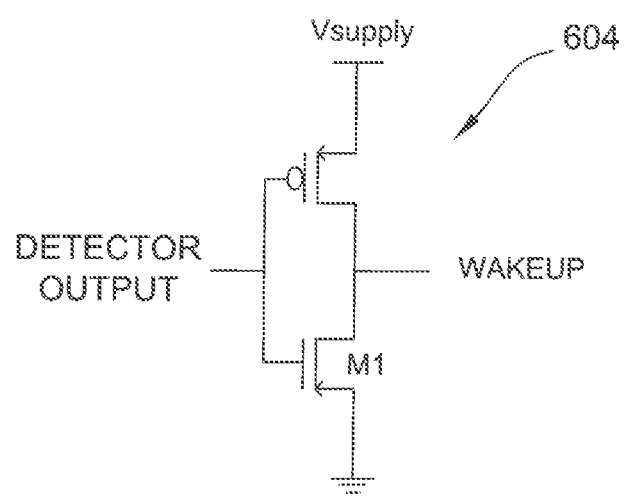

As noted above, because BLE transceivers generally require an activation, or wakeup voltage of at least 1.8 V, detector network 400 includes inverter 414. Inverter 414 may be implemented in a number of different ways. For example, FIG. 6A is a schematic circuit diagram of a bipolar junction transistor (BJT) inverter 602 that may be used as inverter 414, and FIG. 6B is a schematic circuit diagram of a complementary metal-oxide-semiconductor (CMOS) inverter 604 that be used as inverter 414. BJT inverter 602 and CMOS inverter 604 may be used, for example, if the output of full-wave rectifier 412 is 600 millivolts (mV) or greater.

Figure 7:
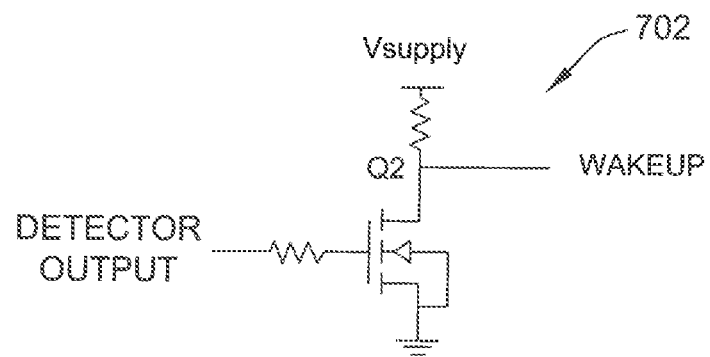
FIG. 7 is a schematic circuit diagram of one embodiment of an inverter that may be used with the detector network shown in FIGS. 4 and 5.

FIG. 7 is a schematic circuit diagram of a low-threshold field effect transistor (FET) inverter 702 that be used as inverter 414. FET inverter 702 may be used, for example, if the output of full-wave rectifier 412 is in a range from approximately 300 mV to 600 mV.

Figure 8:
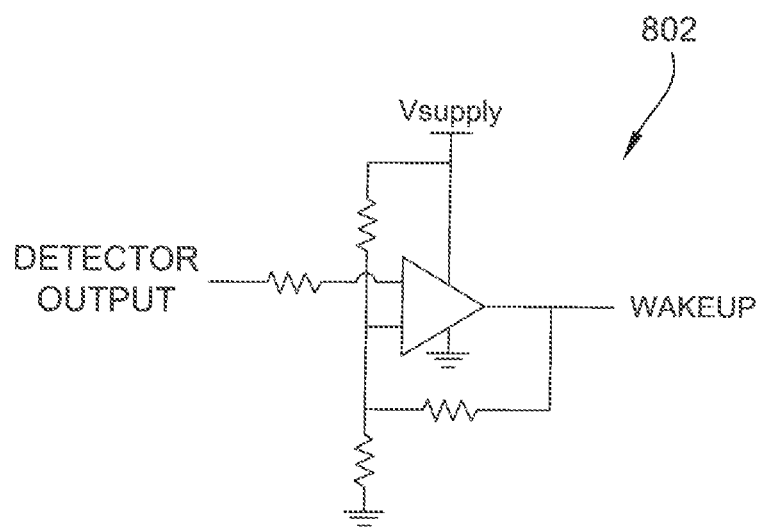
FIG. 8 is a schematic circuit diagram of one embodiment of an inverter that may be used with the detector network shown in FIGS. 4 and 5.

If the output of full-wave rectifier 412 is less than 300 mV, a comparator may be required. Accordingly, FIG. 8 is schematic circuit diagram of a comparator inverter 802 that be used as inverter 414. Comparator inverter 802 is capabie of generating an activation signal for BLE transceiver 402 when the output of full-wave rectifier 412 is as low as approximately 30mV.

Using detector network 400, in one embodiment, it was experimentally determined that sending an NFC signal at a distance of 2 cm resulted in a received signal strength of 13.28 V, sending an NFC signal at a distance of 3 cm resulted in a received signal strength of 3.36 V, and that sending an NFC signal at a distance of 5 cm resulted in a received signal strength of 0.988 V. Notably, these voltage amplitudes are sufficient for any of the inverter types described in FIG. 6A-8.

Embodiments of the present disclosure provide several advantages over known devices. For example, embodiments described herein provide a detector network for an implantable medical device that is capable of using Bluetooth Low Energy (BLE) communications and NFC. In the systems and methods described herein, a voltage detector is activated in the presence of an NFC field and triggers BLE circuitry to activate (or wakeup) to begin normal operations. The detection techniques described herein are passive, and accordingly, consume essentially no current. Therefore, the entire BLE activation process may be achieved with minimum drain on a battery of the implantable medical device, extending the longevity of the battery.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable medical device comprising:
   a housing;
   a cover coupled to the housing and enclosing a region along an exterior of the housing;
   a detector network positioned within the housing;
   a near field communications (NFC) antenna positioned within the cover, the NFC antenna having a loop and a connector extending from the loop, the connector being electrically connected to the detector network at an end distal the loop;
   a Bluetooth low energy (BLE) antenna positioned within the cover, the BLE antenna being C-shaped and having a first end and a second end, the second end being electrically connected to the detector network;
   the detector network comprising:
      a BLE transceiver;
      a BLE path electrically connecting at least the BLE antenna to the BLE transceiver and configured to communicate BLE signals received at the BLE antenna to the BLE transceiver; and
      an NFC path electrically connecting at least the NFC antenna to the BLE transceiver, the NFC path configured to generate an activation signal for the BLE transceiver based on an NFC signal received at the NEC antenna.

2. The implantable medical device of claim 1, wherein the BLE path comprises a trap configured to prevent NFC signals from reaching the BLE transceiver via the BLE path.

3. The implantable medical device of claim 2, wherein the NFC path comprises:
   a resonant tank configured to draw the NFC signal; and
   a full-wave rectifier configured to generate the activation signal based on the NFC signal.

4. The implantable medical device of claim 3, wherein the NFC path further comprises a high voltage protection circuit configured to prevent high voltage NFC signals from damaging at least a portion of the detector network.

5. The implantable medical device of claim 4, wherein the NFC path further comprises an inverter configured to condition the activation signal generated by the full-wave rectifier before providing the activation signal to the BLE transceiver.

6. The implantable medical device of claim 5, wherein the inverter comprises one of a bipolar junction transistor inverter and a complementary metal-oxide-semiconductor inverter.

7. The implantable medical device of claim 5, wherein the inverter comprises a field effect transistor inverter.

8. The implantable medical device of claim 5. wherein the inverter comprises a comparator inverter.

* * * * *